US011471146B2

(12) United States Patent
Petry et al.

(10) Patent No.: US 11,471,146 B2
(45) Date of Patent: Oct. 18, 2022

(54) CERCLAGE SUTURE TENSIONER AND METHODS OF TENSIONING

(71) Applicant: Arthrex, Inc., Naples, FL (US)

(72) Inventors: Andrew C. Petry, Naples, FL (US); John D. Paterson, Naples, FL (US); Steven L. Vander Meulen, Fort Myers, FL (US)

(73) Assignee: Arthrex, Inc., Naples, FL (US)

( * ) Notice: Subject to any disclaimer, the term of this patent is extended or adjusted under 35 U.S.C. 154(b) by 596 days.

(21) Appl. No.: 16/528,960

(22) Filed: Aug. 1, 2019

(65) Prior Publication Data

US 2019/0350578 A1    Nov. 21, 2019

Related U.S. Application Data

(62) Division of application No. 15/276,106, filed on Sep. 26, 2016, now Pat. No. 10,405,847.

(51) Int. Cl.
*A61B 17/04*    (2006.01)

(52) U.S. Cl.
CPC .. *A61B 17/0401* (2013.01); *A61B 2017/0403* (2013.01); *A61B 2017/0414* (2013.01); *A61B 2017/0496* (2013.01)

(58) Field of Classification Search
CPC . A61B 17/04; A61B 17/0401; A61B 17/0469; A61B 17/0482; A61B 17/0483; A61B 2017/0496; A61B 2017/0474; A61B 2017/0414; A61B 2017/0403
See application file for complete search history.

(56) References Cited

U.S. PATENT DOCUMENTS

| | | | |
|---|---|---|---|
| 3,959,960 A | 6/1976 | Santos | |
| 5,275,614 A | 1/1994 | Haber et al. | |
| 5,368,215 A | 11/1994 | Green et al. | |
| 5,935,133 A | 8/1999 | Wagner et al. | |
| 5,944,739 A | 8/1999 | Zlock et al. | |
| 7,081,124 B2 | 7/2006 | Sancoff et al. | |
| 7,326,222 B2 | 2/2008 | Dreyfuss et al. | |
| 8,298,247 B2 | 10/2012 | Sterrett et al. | |
| 8,469,966 B2 | 6/2013 | Allen et al. | |
| 8,469,967 B2 | 6/2013 | Pratt et al. | |
| 8,771,352 B2 | 7/2014 | Conner et al. | |
| 8,939,999 B2 | 1/2015 | Sterrett et al. | |
| 2003/0208210 A1* | 11/2003 | Dreyfuss | A61B 17/0483 606/144 |
| 2009/0326538 A1 | 12/2009 | Sennett et al. | |
| 2011/0029079 A1 | 2/2011 | Paulos | |
| 2012/0157765 A1 | 6/2012 | Mitelberg | |
| 2014/0296881 A1* | 10/2014 | Ranucci | A61B 17/0401 606/144 |

* cited by examiner

*Primary Examiner* — Vi X Nguyen
(74) *Attorney, Agent, or Firm* — Potomac Law Group, PLLC

(57) ABSTRACT

A surgical tensioner and methods for surgical repairs. A tensioner can tension a flexible strand (suture or wire) attached to tissue (for example, graft or bone segments). A tensioner can include an angled tip with a split hole to past-point on a knot and lock the construct during tensioning. A tensioner can include a securing mechanism that can capture a flexible strand and lock it into place.

11 Claims, 5 Drawing Sheets

Section B-B

CERCLAGE SUTURE TENSIONER AND METHODS OF TENSIONING

CROSS-REFERENCE TO RELATED APPLICATIONS

The present application is a Divisional of U.S. patent application Ser. No. 15/276,106, filed Sep. 26, 2016, the disclosure of which is incorporated herein by reference in its entirety.

BACKGROUND

The disclosure relates to surgical instruments and methods for tensioning of flexible materials and, more specifically, to a novel tensioning device.

SUMMARY

A surgical tensioner and methods for surgical repairs are disclosed. A tensioner can tension a flexible material or strand (suture, wire or fabric) attached to tissue (for example, graft or bone segments). A tensioner can include an angled tip with a plurality of passages (for example, a split hole) to past-point on a knot and lock the construct during tensioning. A tensioner can include a securing mechanism that can capture a flexible strand and lock it into place.

Methods of tensioning are also disclosed. In an embodiment, flexible material can be tensioned with a tensioner by passing limbs of the flexible material through separate passages within an angled tip of the instrument; and tensioning the limbs.

BRIEF DESCRIPTION OF THE DRAWINGS

FIG. 4(*a*) illustrates an exemplary angled tip of a suture tensioner.

FIG. 4(*b*) illustrates another exemplary angled tip of a suture tensioner.

DETAILED DESCRIPTION

Figure 1:
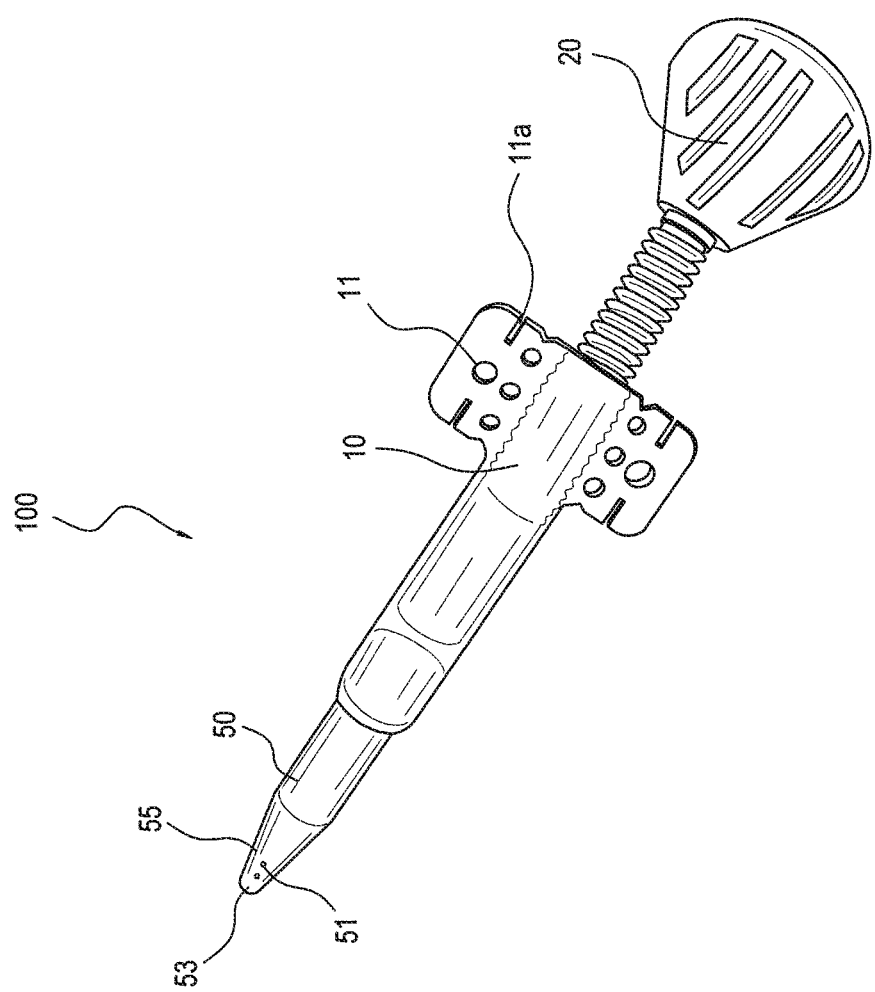
FIG. 1 is a perspective view of a suture tensioner according to an exemplary embodiment.

The disclosure provides a tensioner used for applying tension to a length of flexible material, for example suture such as high strength suture, tape, wire, cable, or fabric. The tensioner includes a tip with a plurality of passages that allow a plurality of limbs to be fed through the plurality of passages at the tip. The tip may be angled. The passages may be adjacent and contacting each other, or may be spaced from each other. The flexible material may be tied and then both limbs may be passed through the tip of the tensioner. The limbs may be secured to a securing device (for example, cleated on a paddle) and then tensioned by actuating an adjustment device (for example, twisting a handle). Turning the adjustment device draws against the flexible material, increasing therefore the tension on both limbs. The tensioner may be employed in conjunction with a tensiometer. The tensiometer indicates how much force is being applied to the construct. The tensioner past-points the flexible material on a knot.

A tensioner can include an angled tip having a non-vertical most distal end surface communicating with a plurality of apertures, openings, or passages, to allow a plurality of suture limbs to past-point the suture on a knot. An angled tip may include two suture passages or openings communicating with a most distal non-vertical surface of the angled tip. The two suture passages or openings may be adjacent and contacting each other, or may be spaced apart from each other, and may have the same or similar diameters and/or configurations. An angled tip may be stationary or rotating. A rotating tip design allows the tip to spin/rotate independently of the external driver/shaft to keep its position without twisting the suture. The stationary tip allows the driver/shaft to spin internally independent of the tip without twisting the suture. In this manner, the device allows tensioning of a suture construct around a bone with or without tissue fixation to reduce or approximate a bone fragment, close a fracture site, or compress soft tissue in place by tightening a knotted sequence to tension and lock a suture in place while being capable of measuring the tensioning force applied.

In an embodiment, a tensioner comprises: a shaft having a longitudinal axis, a distal end, and a proximal end; and a tip at a most distal end of the shaft, the tip having a plurality of passages to allow a plurality of limbs of a flexible material to pass therethrough. The tensioner may further comprise a securing mechanism to allow secure placement of the limbs; and an adjustment device to exert a desired tension on the plurality of limbs. The flexible material may be suture, tape, wire, cable, fabric or any known material used for cerclage (i.e., that may be optionally wrapped around a bone or bone fragment). The tensioner may comprise two passages to allow two limbs of flexible material to pass therethrough, each limb through a separate passage.

In another embodiment, a tensioner comprises: a shaft having a longitudinal axis, a distal end, and a proximal end; a cannulated body with a securing mechanism (for example, a thumb pad with cleats), the cannulated body housing at least a part of the shaft; a spring; a cannulated tube; a handle; and a tip at the distal end of the shaft, the tip having a plurality of adjacent passages/openings/apertures to allow a plurality of limbs of flexible material to pass therethrough, the tip being provided with a most distal end surface that is non-vertical relative to the longitudinal axis of the shaft. The flexible material may be suture, tape, wire, cable, fabric or any known material used for cerclage (i.e., that may be wrapped around a bone or bone fragment). The plurality of limbs may be passed through at least a portion of the shaft and cannulated body.

Methods of tensioning flexible strands such as sutures, wires, tapes, cables or fabrics are also disclosed. In an embodiment, a flexible material can be tensioned with a tensioner by passing limbs of the flexible material through passages/apertures/openings within a tip of the tensioner; and tensioning the limbs. Tensioning of the limbs may be conducted simultaneously or sequentially. The limbs may be further passed through at least a portion of a cannulation of the tensioner. The flexible material may be suture, tape, wire, cable, fabric or any known cerclage material.

A method of tissue fixation (for example, graft or bone fixation) includes wrapping the tissue (for example, a graft or fractured bone) with a length of flexible material (for example, suture such as high strength suture material) and securing the flexible material to the tissue. The flexible material may be secured by tying one or more knots, for example, by forming one or more slip knots in the length of flexible material. Both legs of the flexible material (both post legs) may be threaded through the tip of the device. In an embodiment, each post leg is passed through one of the two passages/apertures/openings communicating with the most distal end of the tip. Each post leg may then be passed through at least a portion of a cannulated tube of the tensioner and then secured to a securing mechanism, for example, secured into a forked pin attached to an adjustment device, or cleated on a paddle. Turning the adjustment device (for example, a wheel or a knob or a handle) pulls both limbs taut and exerts tension on both legs/limbs of the flexible material. A scale may be provided on the tensioner to indicate the relative and desired amount of tension being applied. The tension to be applied by the surgeon on the flexible material depends on the tissue characteristics (for example, the bone quality) and other factors. The flexible material may be suture, tape, wire, cable, fabric or any known cerclage material.

The disclosure also provides a method of tissue fixation (for example, graft or bone fixation) that includes wrapping the tissue (for example, a graft or fractured bone) with a length of flexible material (for example, suture such as high strength suture) and forming a knot in the length of suture. A post leg of the length of suture is threaded through a first passage extending from a first surface of the angled tip to a second surface of the angled tip of a tensioner. The other post leg of the length of suture may be threaded through a second passage extending from a first surface of the angled tip to another surface of the angled tip of the tensioner. The post legs may then be optionally passed through at least a portion of a cannulated tube of the tensioner. The two post legs may be threaded simultaneously or sequentially. The post legs may be secured into a securing mechanism (for example, cleats that allow the legs to easily wrap around). Turning an adjustment device (for example, a wheel, a knob or a handle) pulls both suture legs taut and exerts tension on the suture. A scale may be provided on the tensioner to indicate the relative amount of tension being applied. The tension to be applied by the surgeon on the suture depends on the tissue characteristics (for example, the bone quality) and other factors.

The instruments and methods of the present disclosure provide apparatus and methods for tensioning suture attached to tissue (for example, graft or bone segments).

A surgical technique for attaching two sections of tissue, or for encircling a bone or bone fragment(s), with a high strength suture material is disclosed. Instruments and methods for repairing a bone fracture or for attaching two sections of tissues where placement of a suture, wire or cable is conducted without the tissue damage and irritation presented using cerclage wires are also disclosed. The instruments and devices disclosed herein are indicated for bone fixation using suture or cerclage wire, which is a surgical procedure for securing fractured or weakened bone. Procedures in which bone cerclage may be indicated include, for example, humeral stem fracture repair and total shoulder surgery. After the cerclage limb strands are tensioned and wrapped, excess flexible material is cut off.

Referring now to the drawings, where like elements are designated by like reference numerals, FIGS. 1-8 illustrate various structural components of tensioner 100, 200 (instrument 100, 200; suture tensioner 100, 200; tensioning device 100, 200; or suture tensioning device 100, 200) of the present disclosure. FIGS. 9-15 illustrate steps of a method of cerclage and tensioning with the tensioner 100, 200.

Figure 2:
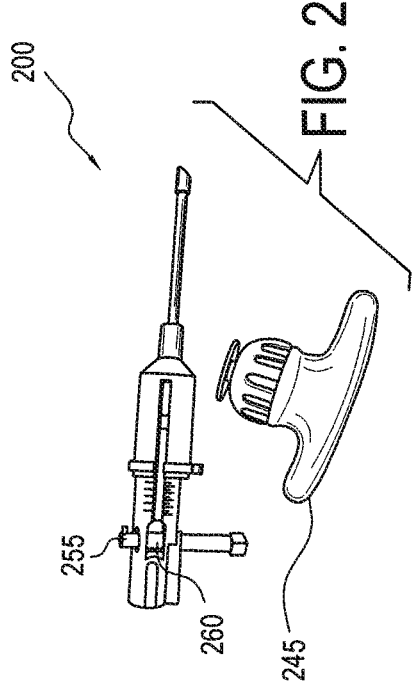
FIG. 2 is a perspective view of a suture tensioner according to another exemplary embodiment.

FIG. 1 illustrates exemplary tensioner 100 which is a single-use disposable instrument or device. FIG. 2 illustrates another exemplary tensioner 200 which is a reusable multiple-use instrument or device with a built-in tensiometer.

Figure 3:
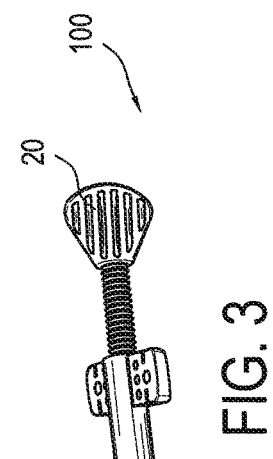
FIG. 3 is another perspective view of the suture tensioner of FIG. 1.

FIGS. 1 and 3 illustrate different views of tensioner 100 which has a design with a threaded core to tension limbs of flexible material (suture). As detailed below, the tensioner 100 is also provided with cleats to easily wrap and hold flexible material.

Tensioner 100 includes a cannulated elongated body 10 with thumb pad 11 with a plurality of cleats or slits 11a, a handle 20 with exterior threads 22, a shaft 30, an internal spring 33, a cannulated tubular member 40, and a tip 50 with angled tip 55 having a plurality of passages or openings 51, 53. Details of exemplary tensioner 100 are illustrated in FIGS. 5-8.

Tubular member 40 is provided with a plurality of outer tension measurement markings 44 (FIGS. 5 and 8) to indicate the tension force. Internal spring 33 measures the tension force applied to the suture limbs.

Figure 5:
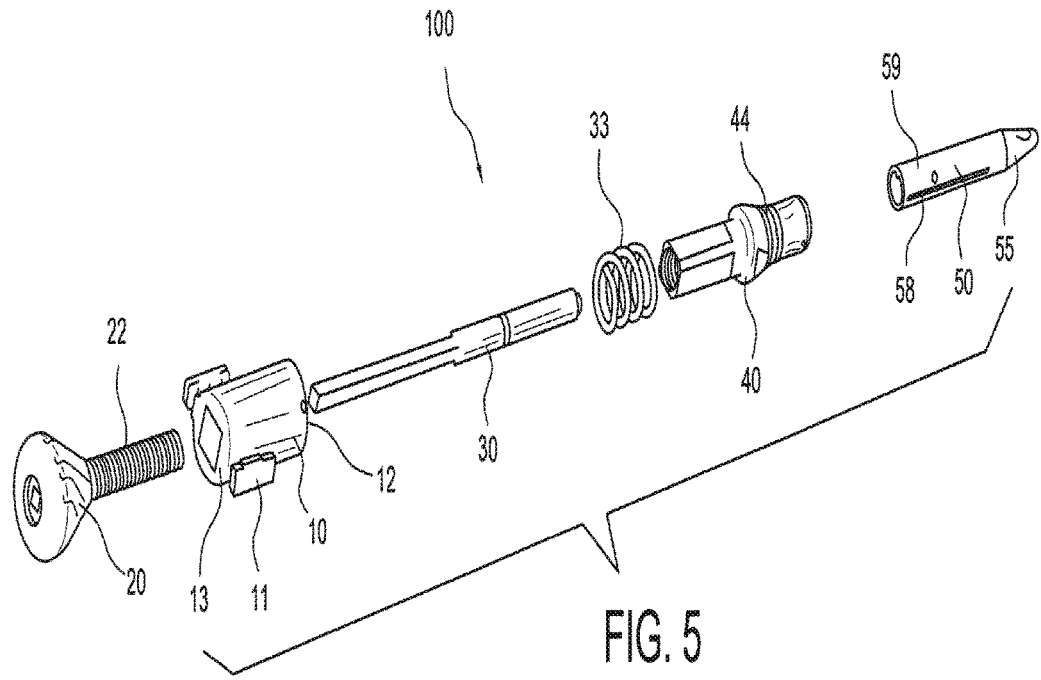
FIG. 5 is an exploded view of the suture tensioner of FIG. 1.
Figure 6:
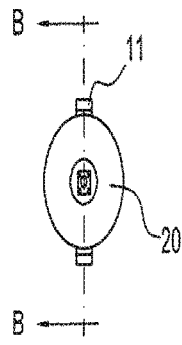
FIG. 6 is left side view of the distal end of the suture tensioner of FIG. 5.
Figure 7:
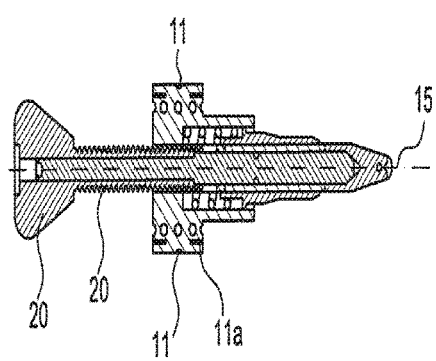
FIG. 7 is a cross-sectional view of the suture tensioner of FIG. 6, taken along line B-B.
Figure 8:
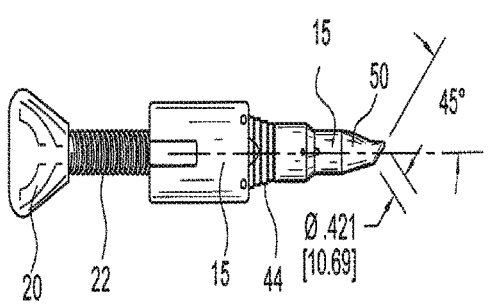
FIG. 8 is a front side view of the suture tensioner of FIG. 5.

Cannulated body 10 has a distal end 12 and a proximal end 13, as shown in FIG. 5. The body 10 of the tensioner 100 includes a cannulated shaft or tube section that allows shaft 30, spring 33 and cannulated tubular member 40 to be received therein.

Figure 4:
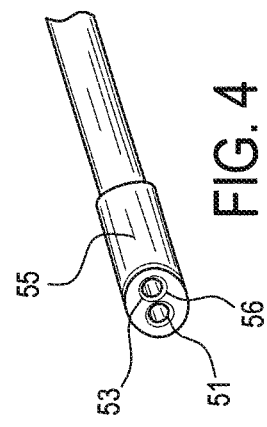
FIG. 4 is an enlarged perspective view of the distal end of the suture tensioner of FIG. 1.

As more clearly shown in FIG. 5, tip 50 includes a cannulated shaft 59 which is provided with longitudinal slits or slots 58 having a specific configuration and dimensions that allow a flexible strand (for example, suture strand or suture tape) to freely pass through cannulated shaft of the tip. Tip 50 includes an angled tip 55 (angled tip portion 55 or angled tip region 55) having a plurality of passages 51, 53. Angled tip portion 55 of the instrument 100 is illustrated in more detail in FIGS. 4, 4(a) and 4(b). FIG. 4 illustrates a split hole design to past point a knot (for example, a half-hitch) and lock the construct during tensioning. This concept may apply to all tensioners contemplated by the present disclosure, including tensioners 100, 200.

Figure 4B:
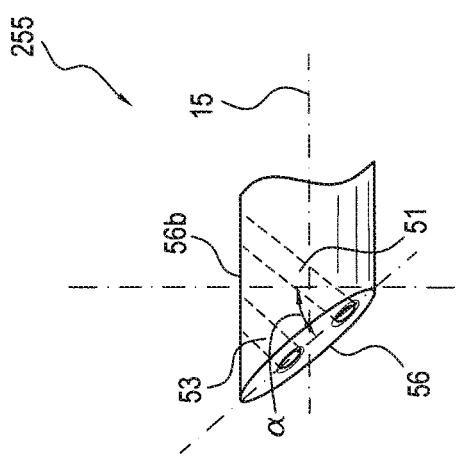
Figure 4A:
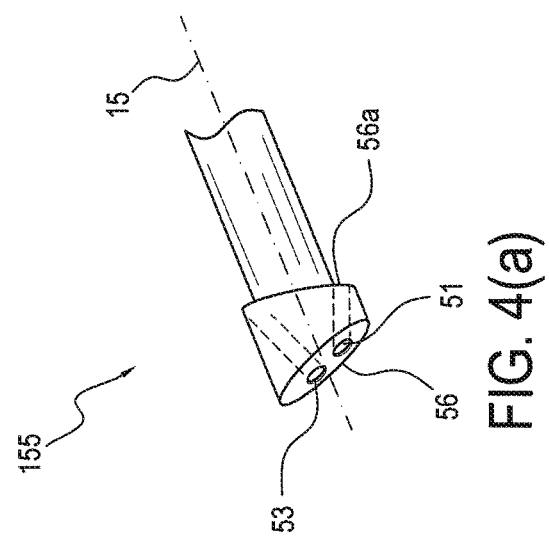

Angled tip portion 55 is provided with a most distal surface 56 that is angled relative to longitudinal axis 15 of body 10 (which coincides with the longitudinal axis of tubular member 40, shaft 30 and cannulated shaft 59). Most distal surface 56 is non-vertical relative to axis 15 and forms an angle other than 90 degrees with axis 15. For example, as shown in FIG. 4(b), angle α may be of about 45 degrees.

Passages 51, 53 (openings, apertures or holes 51, 53) extend from the most distal surface 56 of the angled tip portion 55, into cannulation of the shaft 59, and to another surface 56a, 56b of angled tip 55. Passages 51, 53 are through-openings or through-passages that allow limbs of flexible materials to easily pass therethrough. Passages 51, 53 may contact each other or may be adjacent to each other or spaced apart from each other. Passages 51, 53 may have similar or different dimensions and/or profiles. Passages 51, 53 may be located symmetric relative to longitudinal axis 15 of the tensioner or asymmetric. The exemplary embodiment illustrated in FIG. 4 shows passages 51, 53 as adjacent, symmetrically located relative to axis 15, and as having same dimension and profiles. Passages 51, 53 may be beveled to allow easy passage of flexible strands (sutures). Passages 51, 53 may be parallel to each other (i.e., each of their longitudinal axis forms an angle with the longitudinal axis 15 of the instrument and about 0 angle between their longitudinal axis). In an exemplary embodiment, passages 51, 53 are two holes for separate suture limbs to past point and tension knot. The angled tip design allows for past point of knot on suture construct, i.e., pushes one of the suture limbs (one of the limbs of the flexible material) past the knot, to tighten and lock down the knot. For the knot to be tensioned down and locked, the limbs need to be spread above the knot (and not pulled in a direction directly perpendicular to the knot). By angling the distal surface 56, the distance between the two suture limbs (between the two strands/limbs of flexible material extending from the knot) is spread enough to create the past-point effect or result.

The angled tip may be free to rotate independent of the body and shaft of the instrument, or may be stationary. For example, FIG. 4(*a*) illustrates a rotary tip 155 with passages 51, 53 that extend from most distal surface 56 of the tip to another surface of the tip, for example, surface 56*a* which is opposite to surface 56, and are not parallel to each other, yet are symmetric relative to each other and to the longitudinal axis 15 of the tensioner. FIG. 4(*b*) illustrates an exemplary stationary tip 255 with passages 51, 53 extending from most distal surface 56 into the body of the tip and out to another surface of the tip, for example, outer surface 56*b* of the tip. In this exemplary embodiment, passages 51, 53 are about parallel to each other and extend in a direction about perpendicular to the most distal surface 56 of the tip 255.

Cannulated elongated body 10 is provided at its proximal end 13 with a handle 20, as shown in FIGS. 1-3. Handle 20 is assembled onto proximal end 13 of the body 10 as shown in FIG. 5. Handle 20 is cannulated to allow rotatable engagement with shaft 30 (to house at least a portion of shaft 30) which in turn is received within the cannulation of body 10.

FIG. 2 illustrates another exemplary embodiment of tensioner 200 of the present disclosure. Tensioner 200 is similar to tensioner 100 described in detail above, except that the configuration of the adjustment device is different (i.e., the handle with threaded core to tension and the cleats on the thumb pad of tensioner 100 are replaced by a knob 245 and ratcheting handle 255 with a tensioner crank slot 260 of tensioner 200). Knob 245 of tensioner 200 is configured to be removed from the device, to allow passage of at least one suture strand through the slit, and to be subsequently reinserted over the fed suture strand. The simple crank mechanism allows suture limbs to wrap around and be tensioned. Ratcheting handle 255 allows easy tension control. Tensioner 200 is a reusable tensioner.

In use, knob 245 is first removed from the tensioner 200 by actuating the knob in a first direction. Subsequently, limbs of flexible material such as suture (for example, a first limb and a second limb of a graft passing suture which exits percutaneously after the graft is pulled into a femoral or tibial socket; or limbs of suture wrapped and tied around bone) are fed through the passages 51, 53 of the tip of the device so that the limbs pass through the tip and through longitudinal slits of the cannulated tube and are secured into a forked pin attached to the knob 245. The knob 245 is then reinserted over the fed suture limbs by actuating the knob in a second direction, which may be different from the first direction. The knob can be released by either pushing the lever or by pulling the knob out of the device. Turning the knob counterclockwise draws against the suture limbs, increasing therefore the tension on the suture. The tensioner 200 may be employed in conjunction with a tensiometer, or may be provided with a built-in tensiometer.

The present disclosure may be used to secure any type of tissue, for example bone, cartilage, ligament, graft or tendon, such as a biceps tendon or a rotator cuff, which require suture attachment and appropriate tension, or to encircle a bone or bone fragment, or to attach tissue to another tissue.

An exemplary method of tissue repair 300 using a tensioner such as tensioner 100, 200 of the present disclosure is illustrated with reference to FIGS. 9-15. The steps detailed below with reference to FIGS. 9-15 illustrate a cerclage repair with a flexible material in the form of an exemplary suture tape such as FiberTape® employed with a passing instrument (for example, a needle such as a blunt cerclage passing needle) and with tensioner 100, 200.

Figure 9:
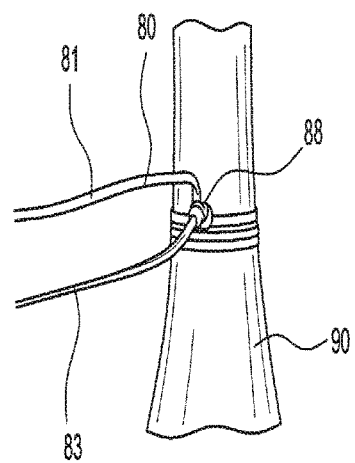
FIGS. 9-15 illustrate an exemplary method of cerclage repair with a suture tensioner.

FIG. 9 illustrates flexible member 80 passed around exemplary tissue 90 (bone 90) with a suture passer instrument such as a needle (not shown). Flexible member 80 may be passed at least once, preferably at least twice, around bone 90. Flexible member 80 may be first folded and then wrapped around the bone 90. Flexible member 80 may be wrapped at least once, preferably at least twice, around the bone 90. A suture passer such as a needle (for example, a blunt curved needle with two adjacent eyelets provided at one end of the needle) may be employed to pass flexible member 80.

Flexible member 80 may be suture in the form of a suture tape such as FiberTape® 80 which is secured to bone 90 with knot 88 (for example, a pre-tied racking hitch 88). FIG. 9 also illustrates limbs or tails 81, 83 (FiberTape® limbs or tails 81, 83) and half-hitch knot 89 tied behind racking hitch 88. The half-hitch 89 may be hand tightened to prepare for tensioner.

Figure 10:
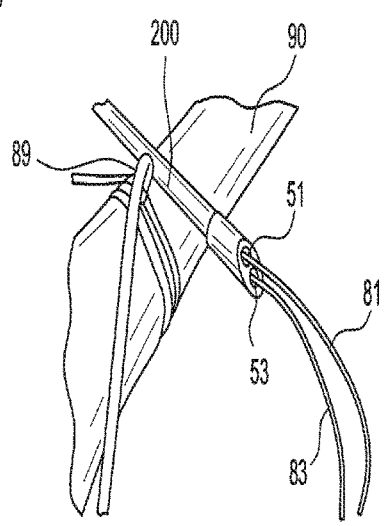

FIG. 10: insert FiberTape® tails 81, 83 into separate passages/holes in tensioner 200 (reusable tensioner 200).

Figure 11:
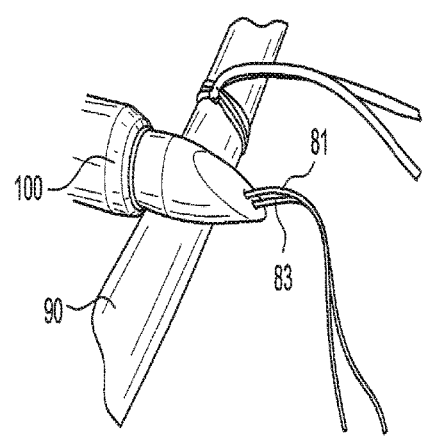

FIG. 11: insert FiberTape® tails 81, 83 into separate passages/holes in tensioner 100 (single-use tensioner 100).

Figure 12:
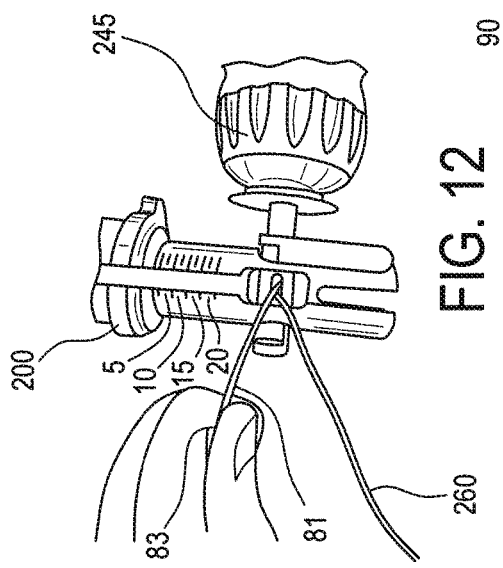

FIG. 12: load FiberTape® tails 81, 83 into tensioner crank slot 260 of tensioner 200 (reusable tensioner).

Figure 13:
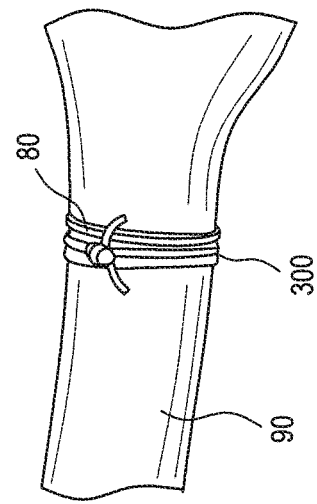

FIG. 13: wrap FiberTape® tails 81, 83 around cleats 11*a* of tensioner 100 (single-use tensioner).

Figure 14:
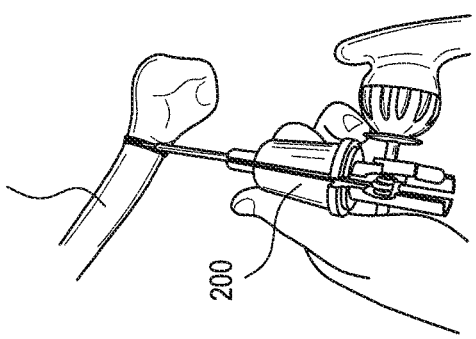

FIG. 14: tighten tensioner 200 to desired FiberTape® tension.

Figure 15:
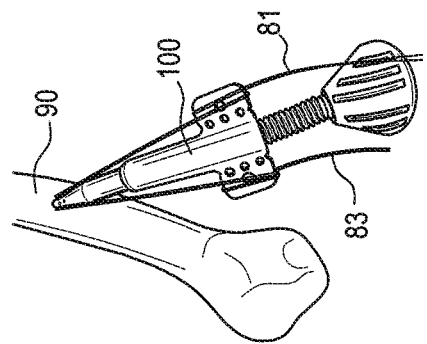

FIG. 15: once tensioned, cut the FiberTape® tails 81, 83 for final repair 300.

An exemplary method of a tensioning technique employed in a graft fixation and tensioning comprises inter alia the steps of (i) providing cerclage material around a bone or bone fragments; (ii) threading at least two limbs of the cerclage material through tip passages 51, 53 of tensioning device 100, 200 described above; and (iii) exerting a desired tension on the limbs of the cerclage material. The cerclage material may be wrapped and tied around the bone. The cerclage material may be tied around the bone with at least one knot. The cerclage material may be wrapped at least once around the bone. The cerclage material may be suture, tape, suture tape, wire, cable, fabric or any known cerclage material.

Another exemplary method of tensioning technique employed in graft fixation and tensioning may comprise the steps of (i) providing graft passing sutures to a graft undergoing graft fixation and tensioning; (ii) threading at least two limbs of the passing sutures through tip passages 51, 53 of tensioner 100, 200 described above; and (iii) exerting a desired tension on the limbs of the passing suture. The graft may be fixed or fixated within the joint (i.e., within the tunnel or socket) with fixation devices known in the art (for example, screws, anchors or buttons) and by known methods in the art.

Another exemplary method of suture tensioning technique employed in graft fixation and tensioning may comprise the steps of (i) wrapping a suture at least once around a bone or bone fragments; (ii) threading limbs of the wrapped suture through tip passages 51, 53 of tensioner 100, 200 described above; and (iii) exerting a desired tension on the limbs. The suture may be secured to the bone by tying at least one knot.

Tensioners 100, 200 described above may be also employed in additional surgical applications that require suture tensioning, for example, in shoulder applications where the device may be employed as both a knot pusher and a suture tensioner.

For the purposes of the present invention, the term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body. In a preferred embodiment of the invention, the suture comprises a high strength suture sold by Arthrex, Inc. under the tradename FiberWire®. FiberWire® suture is formed of an advanced, high-strength fiber material, namely ultrahigh molecular weight polyethylene (UHMWPE), sold under the tradenames Spectra® (Honeywell International Inc., Colonial Heights, VA) and Dyneema® (DSM N. V., Heerlen, the Netherlands), braided with at least one other fiber, natural or synthetic, to form lengths of suture material.

What is claimed is:

1. A tensioner for tensioning limbs of a flexible strand secured to tissue, comprising:

a body having a longitudinal axis, a distal end, and a proximal end; and a tip at the distal end of the body, the tip having a first through-passage and a second through-passage to receive the flexible strand and to allow a first limb of the flexible strand to pass through the first through-passage and a second limb of the flexible strand to pass through the second through-passage.

2. The tensioner of claim 1, further comprising a handle assembly at the proximal end of the body configured to secure and tension the first limb and the second limb.

3. The tensioner of claim 1, wherein the tip is an angled tip with a most distal end surface that forms an angle other than about 90 degrees with the longitudinal axis of the body.

4. The tensioner of claim 1, wherein the flexible strand is suture and the tip includes two suture passages.

5. The tensioner of claim 4, wherein the two suture passages are parallel to each other.

6. The tensioner of claim 4, wherein the two suture passages are non-parallel.

7. The tensioner of claim 1, wherein the handle includes a thumb pad with a plurality of cleats to secure the first limb and the second limb.

8. The tensioner of claim 1, wherein the tip is rotatable relative to the body.

9. The tensioner of claim 1, wherein the tip is stationary and integral with the body.

10. The tensioner of claim 1 further comprising a spring, a tubular member, and a shaft, wherein the spring and at least a portion of the tubular member and at least a portion of the shaft are housed within the body.

11. The tensioner of claim 1, wherein the first limb and the second limb are sutures, tapes, wires, or cables.

* * * * *